US00PP35800P2

(12) United States Plant Patent
Hansen

(10) Patent No.: US PP35,800 P2
(45) Date of Patent: May 7, 2024

(54) ***MONARDA* PLANT NAMED 'Red Velvet'**

(50) Latin Name: ***Monarda* hybrid**
Varietal Denomination: Red Velvet

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 54 days.

(21) Appl. No.: 17/803,789

(22) Filed: Nov. 22, 2022

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell

(57) ABSTRACT

A new and distinct variety of ornamental Bee Balm plant named *Monarda didyma* 'Red Velvet' has medium-height, winter-hardy, vigorous clumping habit, with basally branching stems, dark-green foliage with strong resistance to powdery mildew and numerous large flower heads of intense cherry-red-colored flowers creating excellent flower coverage for a long period in the summer. The new plant is attractive and useful in the garden landscape as a specimen, en masse, or as a container plant.

1 Drawing Sheet

Botanical classification: *Monarda* hybrid.
Variety denomination: 'Red Velvet'.

STATEMENT REGARDING PRIOR DISCLOSURES UNDER 37 CFR 1.77(B)(6)

The first non-enabling disclosure of the claimed plant was made on Dec. 1, 2021, in the form of photographs and a brief description on websites operated by Walters Gardens, Inc. and Proven Winners®, followed on Jun. 8, 2022, as a photograph and brief description in the "Walters Gardens 2022-2023 Catalog." Walters Gardens, Inc and Proven Winners® obtained the plant and all information relating thereto, from the inventor. The first sales of the new plant were on Jul. 11, 2022, by Walters Gardens, Inc. to Garden Crossings. No plants of *Monarda* 'Red Velvet' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102(b) exception.

BACKGROUND OF THE INVENTION

The present invention relates to the new and distinct cultivar of Bee Balm plant, botanically known as *Monarda* 'Red Velvet', and hereinafter also referred to solely as the cultivar 'Red Velvet' or the "new plant". The new plant was selected from self-pollination on Jun. 17, 2015, from an unreleased, proprietary hybrid. known only by the hybridizer code 14-5-1 in a designated hybridizing plot of a wholesale perennial nursery in Zeeland, Michigan, USA. The new plant was a single seedling originally selected in the summer of 2017 from the seeds that were sown in the fall of 2015 and the plant was assigned the breeder code of 15-32-60. Further evaluation was performed in the trial fields of a wholesale perennial nursery in Zeeland, Michigan in the summer of 2019.

The new plant has been asexually propagated initially by division in 2017 followed by shoot tip cuttings in 2019 at the same nursery in the greenhouses in Zeeland, MI, and the subsequent asexually propagated plants were found to be stable, true to type, and identical to the original selection.

BRIEF SUMMARY OF THE PLANT

*Monarda* 'Red Velvet' is unique from its parents and all other Bee Balm plants known to the inventor. The nearest comparison varieties are: 'Pardon My Cerise' U.S. Plant Pat. No. 29,234, 'Berry Taffy' U.S. Plant Pat. No. 34,715, 'Cherry Pops' U.S. Plant Pat. No. 27,618, 'Leading Lady Raspberry' U.S. Plant Pat. No. 34,130, 'Pardon My Rose' U.S. Plant Pat. No. 34,434, 'Gardenview Scarlet' (not patented), 'Jacob Cline' (not patented), 'Fireball' U.S. Plant Pat. No. 14,235, and 'Fire Marshall' U.S. Plant Pat. No. 23,286.

'Pardon My Cerise' has a significantly smaller habit with flowers that are deep cherry-red. 'Berry Taffy' has a more compact shorter habit with flowers that are hot raspberry-pink. 'Cherry Pops' has a slightly shorter habit with flowers that are cherry-red. 'Leading Lady Raspberry' has a significantly shorter habit, the flower color is a bright raspberry, and the lower labium has darker spots. 'Pardon My Rose' is significantly smaller in habit, the flowers are intense rose-pink with darker spots in the lower labium. 'Gardenview Scarlet' is significantly taller and less compact in habit. 'Jacob Cline' has a significantly taller and more open habit. 'Fireball' has a shorter habit and reddish-purple flowers. 'Fire Marshall' has a shorter habit with flowers that are a slightly deeper red without spots.

The parent plant has a taller and more open habit and the flower color is light pink and less reddish.

The following are traits of *Monarda* 'Red Velvet' that in combination distinguish it from all other Bee Balm plants known to the inventor:

1. Medium height, winter-hardy, vigorous, clumping habit;
2. Dark-green glossy leaves that are strongly resistant to powdery mildew;
3. Large flower heads of intense, cherry-red-colored flowers for a long period in summer with excellent flower coverage;
4. Flower heads are subtended by wine-colored bracts.

BRIEF DESCRIPTION OF THE DRAWINGS

The photographs of the new plant demonstrate the unique traits of 'Red Velvet' and the overall appearance of a three-year-old plant in the full-sun outdoor research facility of a wholesale perennial nursery in Zeeland, Michigan. The colors are as accurate as reasonably possible with color reproductions. Variations in the ambient light spectrum, source, and direction may cause the appearance of minor variations in color.

DETAILED BOTANICAL DESCRIPTION

Figure 1:
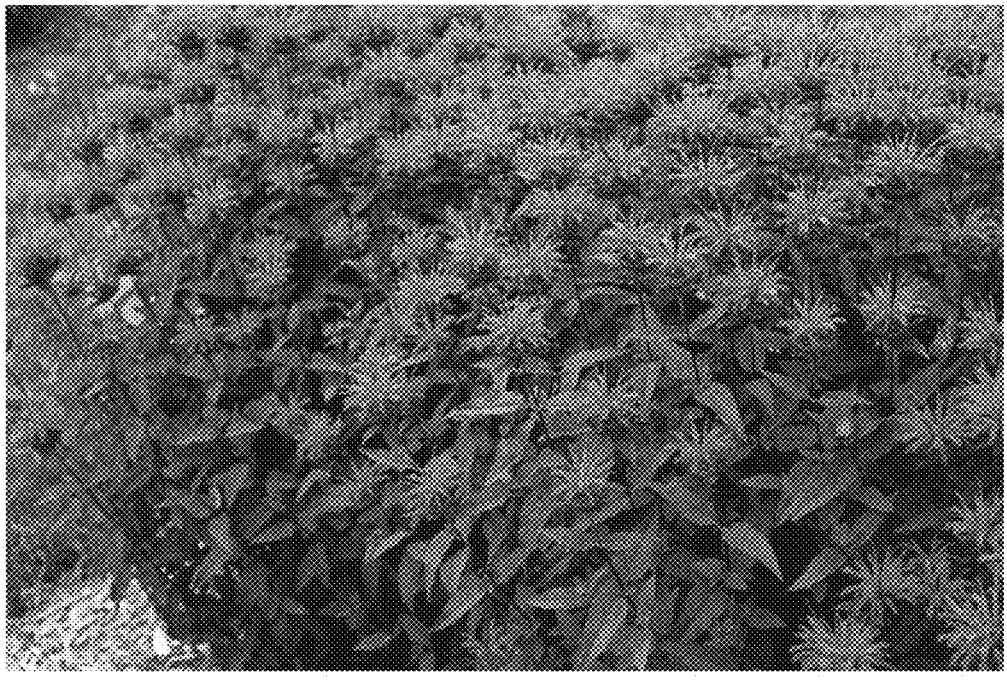
FIG. 1 shows the new plant in flower in the research facility.
Figure 2:
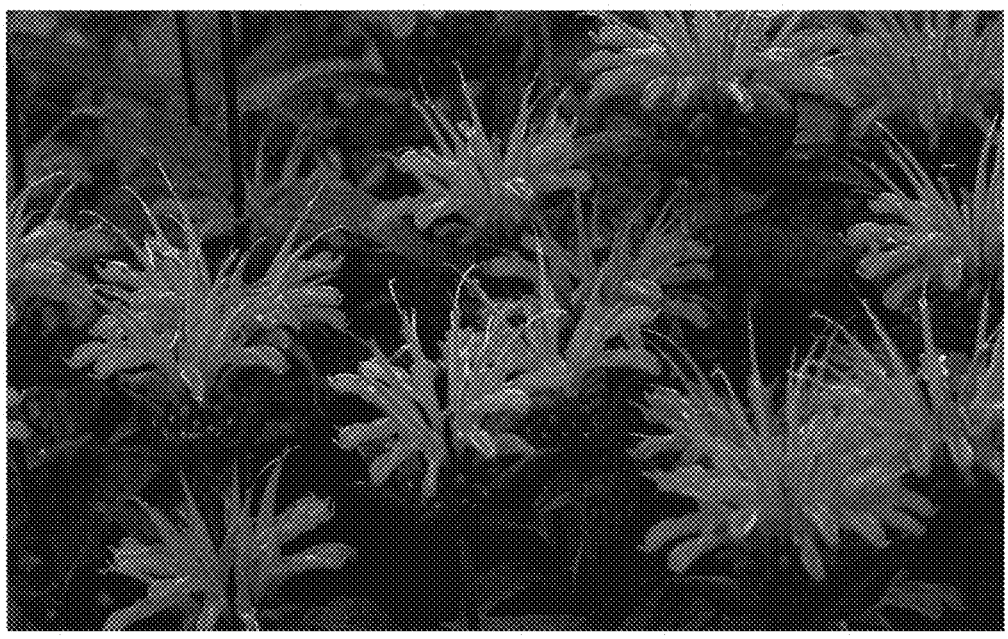
FIG. 2 shows a close-up of the flowers.

The following descriptions and color references are based on the 2015 edition of The Royal Horticultural Society Colour Chart except where common dictionary terms are used. *Monarda* 'Red Velvet' has not been observed under all possible environments. The phenotype may vary slightly with different growing environments such as temperature, light, fertility, soil pH, moisture, and maturity levels, but without any change in the genotype. The following observations and size descriptions are based on two-year-old plants in a display garden at a nursery in Zeeland, Michigan with supplemental fertilizer and water as needed but without plant growth regulators or pinching.

Botanical classification: *Monarda* hybrid including the species *didyma, fistulosa, bradburiana*, and *pringlei;*

Parentage: The parent is the proprietary hybrid known only as 14-5-1;

Plant habit: Winter-hardy herbaceous perennial, compact, producing several stems spreading by short rhizomes; to 80 cm tall at flowering and 77 cm wide; flowering beginning early-summer in Michigan and continuing for about 5 to six weeks;

Propagation: Stem cuttings;

Time to produce finished crop in 3.8-liter pots: About 8 to 10 weeks; vigorous rate of growth;

Root: Fine, fibrous, and freely branching; color creamy white to tau depending on soil type;

Leaves: Simple; lanceolate; opposite; serrated and microciliolate margin; finely and sparsely puberulent above and glabrescent below; slightly lustrous above, matte below; acute apex, rounded to cordate base; to about 78 mm long and about 40 mm wide, decreasing distally, average about 68 mm long and 32 mm wide;

Leaf color: Young expanding leaves between RHS 137B and RHS 146B on adaxial surface and on abaxial surface nearest RHS 146B; mature adaxial leaves between RHS 139A and RHS NN137A and abaxial leaves between RHS 147B and RHS 146A;

Foliage fragrance: Pleasantly herbal;

Veins: Pinnate; minutely puberulent adaxial, pubescent abaxial; slightly sunken above and co state below;

Vein color: Mature adaxial proximal midrib nearest RHS 160D, and proximal and central primary veins and distal midrib nearest RHS N144A; mature abaxial midrib nearest RHS 145D, abaxial veins nearest RHS 148C; emerging adaxial midrib and primary veins nearest RHS 146C, emerging abaxial surfaces nearest RHS 147C;

Petiole: Puberulent; slightly concavo-convex; to about 9 mm long and 2 mm across, decreasing distally;

Petiole color: Adaxial nearest RHS 148C without anthocyanin, abaxial center nearest RHS 145C, and margin nearest RHS 137A;

Stems: Quadrangular; puberulent; stiff; flexible; with compound branches starting in distal nodes; to about 6 mm across at base and about 77 cm long; branches to about 30 cm long and 2 mm across at base;

Stem color: Basal portion between RHS 146C and RHS 138B, distal portion in higher sun exposure nearest RHS 146B with light anthocyanin blush of nearest RHS N187C with the greater blush in regions of higher sun exposure;

Branches: In distal nodes; quadrangular; puberulent; vertical; typically, four compound branches per main stem at initial flowering; about 2 mm across at base and to about 30 cm long;

Branch color: Proximally between RHS 145A and RHS 146D with moderate to light anthocyanin blush of nearest RHS 187A with greater sun exposure;

Nodes: About 8 to 9 per stem; internode spacing average about 5 cm, shorter proximally;

Node color: Between RHS 146C and RHS 146B with light to moderate anthocyanin blush of nearest RHS N187C;

Inflorescence: Arranged in terminal verticillate head about 95 mm across and 38 mm tall, opening from the center and progressing outwardly and downwardly;

Flowers: Single, bilabiate, actinomorphic flowers, individual flowers to about 44 mm long to exserted stigma; corolla to about 34 mm long, 16 mm tall, and 7 mm across; numerous, about 120 to 250 flowers per head; flower attitude upright in the center of the head to outwardly toward the perimeter, slightly arcuate distally; self-cleaning;

Flower lasting: Individual flowers persisting about 5 days in Michigan, head remains effective for 2 to 3 weeks;

Flower period: Usually late June to late July; about four to five weeks;

Flower fragrance: None observed;

Buds one to two days prior to opening: Narrowly clavate; tubular; rounded apex; arcuate slightly downward in distal half; about 27 mm long, about 3 mm across in the middle and about 5 mm tall;

Bud color one to two days prior to opening: Nearest RHS 60A;

Petals: Bilabiate; fused in proximal 21 mm, split in two in about the distal 14 mm; puberulent abaxial and glabrous adaxial except puberulent in the center 5 mm of corolla tube;

Upper labium: Straight outwardly; folded, or enrolled into a hood about 14 mm long from fusion and 2.5 mm across and 3.0 mm tall just distal fusion;

Upper labium color: Upon opening through dehiscence adaxial between RHS 53C and RHS 59C, abaxial between RHS 53A and RHS 53B; basal 2 mm of corolla tube adaxial and abaxial nearest RHS NN155D; without spots on adaxial and abaxial;

Lower labium: Arcuate downward; about 15 mm long from fusion, comprising three lobes including two side lobes about 2 mm long and 2 mm across having rounded apex, entire margin, and center lobe to about 3 mm long and 2 mm wide, folded back at a right angle, with acute emarginate apex split in the distal 0.5 mm and entire margin;

Lower labium color: Adaxial free portion closer to RHS 53C than RHS 59C with 0.5 to 1 mm diameter spots between RHS 53B and RHS 53A, adaxial fused corolla nearest RHS 59D without spots; abaxial free portion closer to RHS 53C than RHS 59C, without spots, abaxial fused corolla nearest RHS 59D without spots; basal 2 mm of corolla tube adaxial and abaxial nearest RHS NN155D;

Foliar bracts: Two sets, between 5 and 10 in upper set subtending flower head; proximal set, ovate, with acuminate to narrowly acute apex, sessile rounded base, and serrate margin; to about 49 mm long and 20 mm wide; distal set lanceolate to linear with narrowly acute apex, sessile acuminate base, and ciliolate margin; glabrous adaxial, puberulent abaxial; mostly flat to reflexed distally; to about 15 mm long and 4 mm wide;

Foliar bract color: Proximal set adaxial variable, central portion nearest RHS NN137A with basal deltoid region about one-third the length nearest RHS 145C, distally variably blushed to solid RHS N186C; abaxial between RHS 146A and RHS 138A; distal set adaxial and abaxial 3 mm portion strongly blushed to solid nearest RHS N186C; proximal adaxial portion variable between RHS 147D and RHS 148B, and proximal abaxial nearest RHS 147B;

Androecium: Two;

*Filaments*.—Two, to about 36 mm long by 0.3 mm diameter; adnate to inner corolla tube in proximal 17 mm; color distally nearest RHS 64D, fused proximal portion between RHS 53A and RHS 53B.

*Anther*.—Two; connate; oblong-elliptic, dorsifixed, longitudinal; 3 mm by 1 mm; color between RHS 61A and RHS 61B.

*Pollen*.—Abundant, elliptic to globose, less than 0.1 mm; color between RHS 11A and RHS 11B.

Gynoecium: One per flower; to about 42 mm long at maturity, exserted;

*Style*.—About 39 mm by 0.3 mm; color in basal one-third nearest RHS NN155D, middle portion transitioning to nearest RHS N66D, distal 5 mm between RHS 71C and RHS 64A.

*Stigma*.—Split in two in the distal 2 mm, 0.2 mm in diameter; color between RHS 64A and RHS 71C.

*Ovary*.—Ellipsoidal; to about 1 mm long and 0.75 mm wide; color nearest RHS 146D.

*Calyx*.—Tubular to campanulate; consisting of five fused sepals; about 9 mm long and 3 mm diameter at apex with calyx tube base about 1 mm diameter.

Sepals: Five; apiculate apex; margin micro-serrulate; basal 7.5 mm fused forming corolla tube; about 9 mm long and 1 mm across at fusion; glabrous adaxial and abaxial;

Sepal color: Adaxial and abaxial distal free portion nearest RHS N186A; adaxial nearest RHS 138C, with veins nearest 146A, and basal portion nearest RHS 145D; abaxial basal portion nearest RHS 145D, central portion nearest RHS 146D with darker veins distally of between RHS 146A and RHS N186B, and distally with a light to a moderate blush of nearest RHS N186B;

Foliar bracts: Two sets subtending the inflorescence; lower set with 5 to 7 ovate bracts.

Pedicel: Short, cylindrical; glabrous; about 1 mm long and 0.5 mm diameter;

Pedicel color: Nearest RHS 147C;

Peduncle: Pubescent; stiff; strong; erect; quadrangular to about 2 mm across and about 70 mm long from just above last leaves; with compound branches typically flowering after the initial head and extending the flowering period of the plant;

Peduncle color: Variable; between nearest RHS 146C and RHS 146B with light blush nearest RHS N186C;

Fruit: Single nutlet, elliptical, about 1.0 mm long and 0.7 mm wide; color nearest RHS 202A;

Hardiness: The new plant grows best with plenty of moisture and adequate drainage; hardy to at least from USDA zone 4 through 8;

Disease and pest resistance: Demonstrated strong powdery mildew resistance (*Sphaerotheca pannosa* var. *rosae*) in side-by-side comparison less symptomatic than that of 'Petite Delight' U.S. Plant Pat. No. 10,784 and 'AChall' U.S. Plant Pat. No. 19,582.

I claim:

1. A new and distinct cultivar of ornamental Bee Balm plant named *Monarda* 'Red Velvet', as herein described and illustrated.

* * * * *